United States Patent [19]

Szabo

[11] 4,245,105
[45] Jan. 13, 1981

[54] 3-(α-CYANOALKYL)CARBAMYL BENZIMIDAZOLYL CARBAMATES

[75] Inventor: Karoly Szabo, Vienna, Austria

[73] Assignee: Syracuse University Research Corporation, Syracuse, N.Y.

[21] Appl. No.: 721,905

[22] Filed: Sep. 9, 1976

[30] Foreign Application Priority Data

Sep. 17, 1975 [FR] France .................. 75 28458

[51] Int. Cl.³ .......................................... C07D 235/32
[52] U.S. Cl. ................................ 548/306; 424/273 B
[58] Field of Search .................. 260/309.2; 424/273; 548/306

[56] References Cited

U.S. PATENT DOCUMENTS 3,541,213  11/1970  Klopping ........................... 548/306
3,673,210   6/1972  Daum et al. ...................... 260/309.2

FOREIGN PATENT DOCUMENTS 1523597  3/1968  France ............................. 260/309.2

Primary Examiner—Henry R. Jiles
Assistant Examiner—Richard A. Schwartz
Attorney, Agent, or Firm—Beveridge, DeGrandi, Kline & Lunsford

[57] ABSTRACT

Compounds of formula:

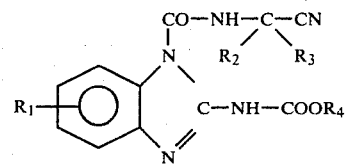

in which
R$_1$ represents a hydrogen or halogen atom, an alkyl group containing from 1 to 4 carbon atoms, an alkoxy group containing from 1 to 4 carbon atoms or a nitro group;
R$_2$ and R$_3$ are the same or different and represent a linear alkyl group having from 1 to 12 carbon atoms, a branched alkyl group having from 3 to 12 carbon atoms, a substituted or unsubstituted aromatic radical containing from 6 to 12 carbon atoms, or forming together with the carbon atom to which they are linked a substituted or unsubstituted cycloalkylene radical, having 3 to 12 carbon atoms; and
R$_4$ represents an alkyl group having from 1 to 4 carbon atoms.

These compounds are systemic fungicides, antisporulants and sterilizers of acaridae eggs.

2 Claims, No Drawings

3-(α-CYANOALKYL)CARBAMYL BENZIMIDAZOLYL CARBAMATES

The present invention relates to new benzimidazole derivatives, their preparation and their use as pesticides.

The compounds according to the invention may be represented by the structural formula (1)

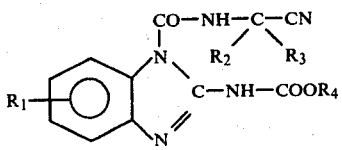
(1)

in which
- $R_1$ represents a hydrogen or halogen atom, an alkyl group containing 1 to 4 carbon atoms, an alkoxy group containing 1 to 4 carbon atoms or a nitro group;
- $R_2$ and $R_3$ are the same or different and represent a linear alkyl group containing from 1 to 12 carbon atoms, a branched alkyl group containing from 3 to 12 carbon atoms, a substituted or unsubstituted aromatic radical containing from 6 to 12 carbon atoms, or together form with the carbon atom to which they are linked to a cycloalkylene radical, substituted or unsubstituted, containing from 3 to 12 carbon atoms; and
- $R_4$ represents an alkyl group containing from 1 to 4 carbon atoms.

Included within formula (1) above are compounds wherein $R_1$ is hydrogen or an alkyl group containing 1 to 4 carbon atoms.

The compounds of formula (1) may be prepared by reacting an isocyanate of the formula (2)

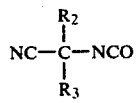
(2)

in which $R_2$ and $R_3$ have the same significance as in formula (1), with an ester of 2-benzimidazolyl-carbamic acid of the formula (3).

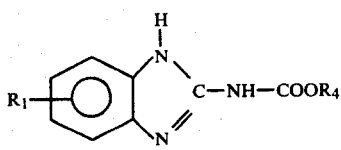
(3)

in which $R_1$ and $R_4$ have the same significance as in formula (1), according to the reaction

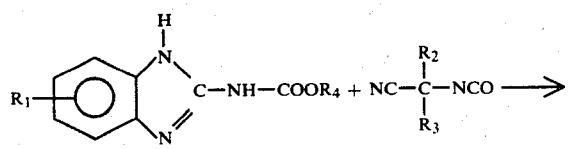

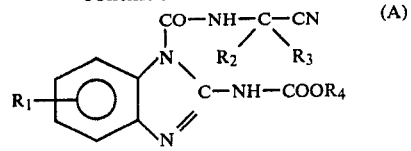
(A)

The isocyanates corresponding to the formula (2) may be obtained by reaction of phosgene on the corresponding α-aminonitriles according to the process described by K. Szabo in U.S. Pat. No. 3,803,208.

The esters of 2-benzimidazolyl-carbamic acid of formula (3) may be prepared by different known processes, in particular described in the U.S. Pat. Nos. 2,933,504 and 3,010,968, the disclosures of which are relied on and incorporated herein for that purpose.

Reaction (A) is effected in an inert solvent such as for example, a chlorinated solvent like methylene chloride, chloroform or carbon tetrachloride, an aliphatic or aromatic hydrocarbon, a carbonyl compound such as acetone or 2-butanone. The temperature of the reaction is between $-10°$ C. and 60° C., preferably between 20° C. and 40° C. Although it is not indispensable, it is possible to operate in the presence of a catalyst known to accelerate the reaction between isocyanates and amines, such as a tertiary amine or a tin compound such as, for example; stannous octoate or dibutyltin dilaurate.

The products of the invention are shown to be systemic fungicides, antisporulants, and sterilizing agents of acaridae eggs.

Compounds of the invention may be used for the treatment of cultivated plants to combat certain parasitic fungi employing dosages that do not harm in any way the plant part treated, whether it be the foliage, the stems, the roots or the seeds. That is, the compounds are used in non-phytotoxic amounts which are effective to produce the intended result. They have the capability of penetrating the treated plants, by way of the roots, leaves, or by seeds. The products are then carried by the rising sap and fluids in the plant and are thus found uniformly distributed throughout the entire plant, even in the parts formed after the treatment. These products, called endotherapic, give to the plant a resistance to all parasitic fungi belonging to a family of well defined types. Fungi of the following species may be combatted according to the invention. Fusarium, Botrytis, Rhizoctonis, Alternaria, Penicillium, Erysiphe, Cercospora, Ustilago, Phomopsis, Venturia, Monilia, Sclerotinia, Coccomyces, Aspergillus, Helminthosporium, Rhizopus, Colletotrichum, Verticillium, Sphaerotheca, Podosphaera, Uninula.

The products of the invention have the original characteristic of being able to control *Ustilago maydis* by preventing this fungus from emitting the disseminating organs which are the sporidii and therefore act as antisporulants.

Finally, the products of the invention, the principal action of which is to destroy the parasitic fungi, possess the additional advantage of being useful on acaridae eggs which they sterilize. This feature is very attractive since with a single treatment one may control two types of very different parasites.

The products according to the invention may be used alone or in admixture with other fungicidal, herbicidal, insecticidal, acaricidal, bactericidal or neumaticidal active materials in all the types of formulation in use in phytosanitary products, such as solutions in an inert organic solvent, solutions in a liquified gas inside an aerosol bomb (the said liquified gas, which is in the gaseous state at normal pressure and temperature, serving also as a propellant), suspensions in water, emulsions in water of solutions in an organic solvent, powders for dusting, wettable powders, pastes and granules.

Examples of inert vehicles which may be used for making the solutions are inert organic solvents including aromatic or aliphatic hydrocarbons such as benzene, toluene, xylene, alkylnaphthalenes, cyclohexane, the paraffins or petroleum fractions, halogenated derivaties of hydrocarbons such as chlorobenzene, chloroethylene, methylene chloride, alcohols such as butanol and glycol and their ethers and esters, ketones, dimethyl formamide and dimethyl sulphoxide. As liquified gases which may be used as solvents may be mentioned the fluorinated halogenated hydrocarbons known by the trademark "Freon".

In the solid formulations, finely divided inert carriers may be used such as chalk, silica, kaolin, clay, talc or diatomaceous earth. When forming emulsions or dispersions, surface-active agents may be introduced therein to homogenize the compositions and to increase their wetting power on the plants, their adhesion and their length of life.

The formulations described above may contain from 0.5 to 95% by weight of the poducts according to the invention. They may be applied directly to the plants, or to the soil adjacent the plant or to the seeds, by the usual methods such as dusting, coating, injection, spraying or as a mist. Customarily, the compounds are diluted so as to obtain a desirable concentration and rate of application, e.g:

10 to 100 g of product according to the invention per hectoliter for spraying treatments.

10 to 50% by weight of product according to the invention for the treatment of seeds.

90 to 95 kg of product according to the invention per hectoliter for applications at very low volume.

For the treatment of soils, for example by injection, the dosage of the product according to the invention used will be from 10 to 200 g per cubic meter of soil. For the treatment of crops by spraying of the ordinary type, the dosage used will be from 100 to 1000 g of product per hectare.

Finally, for the treatment of seeds there will generally ne used 200 g of powder at 10 to 50% of product per qunital (100 lbs) of grains.

The following examples illustrate the present invention.

EXAMPLE 1

130 cc of dry chloroform, 4.5 g of methyl 2-benzimidazolyl-carbamate and 2.9 g of 1-methyl-1-cyano-ethyl-isocyanate are introduced into a reactor. The suspension thus obtained is stirred for a night at the ambient temperature. By filtration a first fraction of 5.2 g of a crystalline product is collected. The solution is then evaporated to dryness and the residue obtained is washed with hexane and dried. 2.1 g of a second fraction of product are thus obtained. The analysis by infrared spectorgraphy (IR) and nuclear magnetic resonance spectrography (RMN) of the two fractions shows that the product in both cases has the formula:

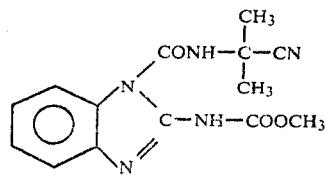

This product melts at 290° C. with incipient decomposition.

EXAMPLE 2

A mixture of 160 cc of dry chloroform, 6 g of methyl 2-benzimidazolyl-carbamate and 4 g of 1-methyl-1-cyano-propylisocyanate is allowed to react overnight at the ambient temperature under the conditions of example 1. 1.5 g of unreacted methyl 2-benzimidazolyl carbamate is obtained on filtration. The solution is then evaporated to dryness and the residue that is obtained is washed with hexane and dried. A solid product in the amount of 7 g is obtained. The IR and RMN analysis show that the product has the formula:

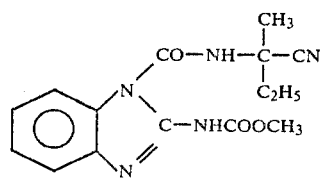

This product melts at 255° C. with incipient decomposition.

EXAMPLE 3

Following the same procedure as in example 1, 500 cc of dry chloroform, 19 g of methyl 2-benzimidazolyl-carbamate and 15 g of 1,3-dimethyl-1-cyano-butyl isocyanate are placed in a reactor. 12.4 g of a solid product are obtained. The IR and RMN analyses show that it has the formula:

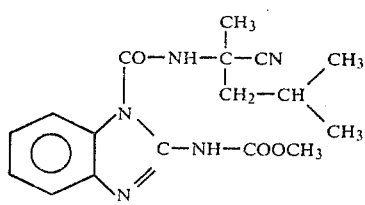

This product melts at 265° C. with incipient decomposition.

EXAMPLE 4

Into a reactor, the following ingredients were charged:

150 cc of dry chloroform, 5.2 g of a mixture containing about 40% of methyl 4-methyl-2-benzimidazolyl-carbamate and about 60% of methyl 5-methyl-2-benzimidazolyl-carbamate (this mixture is obtained by applying the processes described in the patents cited on page 3 to a mixture of 70% of 3,4-diamino-toluene and 30% of 2,3-diamino-toluene) and 3.3 g of 1-methyl-1-cyano-ethyl isocyanate. After stirring for 70 hours at 20° C., the chloroform is evaporated. The residue obtained is washed with hexane and dried. 7 g of a solid product melting at 194° C. are obtained. The analyses by IR and RMN show that it is a mixture containing about 40% of the compound of the formula:

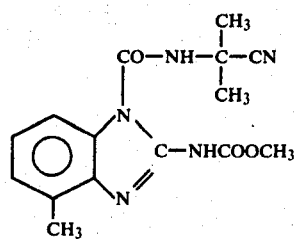

and about 60% of the compound of the formula:

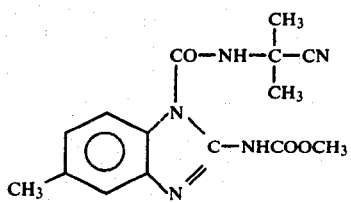

EXAMPLE 5

Using the same conditions as described in example 2, a mixture of 13.2 g of methyl-2-benzimidazolyl-carbamate and 13.9 g of 1-phenyl-1-cyano-ethyl isocyanate is reacted in 400 cc of dry chloroform. 9.3 g of a solid product are obtained. The analyses by IR and RMN show that it has the formula:

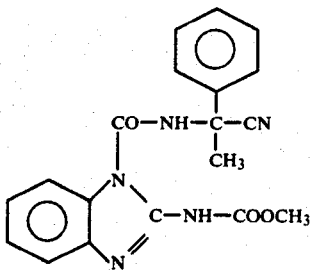

EXAMPLE 6

Following the same process as described in example 2, 22.4 g of methyl-2-benzimidazolyl-carbamate and 20.7 g of 1-cyanocyclohexyl isocyanate are reacted in 700 cc of dry chloroform. 25 g of solid product are obtained. The analyses by IR and RMN show that it has the formula:

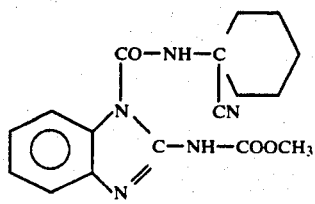

This compound melts at 103° C.

In the Examples 7 to 17 which follow, the fungicidal, antisporulant and sterilizing of acaridae eggs activities of the compounds of the invention are illustrated. In these examples, the dilutions of the compounds are made with water, unless the contrary is mentioned, in the presence of a non-ionic dispersing agent at a concentration of 1%. The tests identified as control tests are made with water containing only dispersing agent.

EXAMPLE 7

Action of the Compounds on Mycoleium Growth

The nutrient medium used is the Czapeck medium of the following composition:

| Sodium nitrate | 2 g |
| --- | --- |
| Dipotassium hydrogen phosphate | 1 g |
| Potassium chloride | 0.5 g |
| Magnesium sulphate (7H$_2$O) | 0.5 g |
| Iron sulphate (7H$_2$O) | 0.01 g |
| Saccharose | 30 g |
| Gelose | 15 g |
| Water q sp | 1000 ml |

The dilutions of the compounds according to the invention are incorporated in this medium maintained in a fused state at 45° C. at the rate of one part by volume to 10 parts of nutrient medium. The dilutions are such that the final concentrations of the compounds in the nutrient medium are as follows:

$C_0 = 0$ ppm (control)
$C_1 = 0.1$ ppm
$C_2 = 0.4$ ppm
$C_3 = 1.6$ ppm
$C_4 = 6.4$ ppm The medium is then run into Petri dishes 90 mm in diameter and allowed to cool and solidify. Each dish is then contaminated with specimens of mycelium removed from fungi cultures aged eight days. These fungi are fusarium, roseum, *rhizoctonia solani* and *phomopsis viticola*.

The dishes are incubated for 2 days in a room maintained at 22° C. and at a relative atmospheric humidity of 70%. After these 2 days, the mycelium has developed creating circular grown-in regions around the contamination point. The diameter of these circular regions were measured.

The results obtained with the compounds of examples 1, 2 and 3 are shown in table No. 1 below. In this table the diameters of the circular regions obtained in the dishes containing the nutrient medium treated with the compounds according to the invention are expressed in a percentage of the diameter of the circular regions obtianed in the control dishes containing the untreated nutrient medium. 0% then represents a total activity, and 100% represents the state of the control test; that is to say, a zero activity.

Table No. I

| | EFFECT ON THE MYCELIUM GROWTH | | | | | | | | | | | |
|---|---|---|---|---|---|---|---|---|---|---|---|---|
| Fungus | Fusarium Roseum | | | | Promopsis Viticola | | | | Rhizoctonia Solani | | | |
| Concentration of the product | 0.1 ppm | 0.4 ppm | 1.6 ppm | 6.4 ppm | 0.1 ppm | 0.4 ppm | 1.6 ppm | 6.4 ppm | 0.1 ppm | 0.4 ppm | 1.6 ppm | 6.4 ppm |
| Product of Example | | | | | | | | | | | | |
| No. 1 | 100 | 100 | 19 | 0 | 70 | 6 | 3 | 3 | 100 | 100 | 19 | 0 |
| No. 2 | 100 | 100 | 80 | 5 | 60 | 33 | 6 | 6 | 100 | 100 | 58 | 0 |
| No. 3 | 100 | 100 | 71 | 0 | 80 | 30 | 10 | 8 | 100 | 86 | 88 | 0 |
| Control | | 100 | | | | 100 | | | | 100 | | |

EXAMPLE 8

Inhibiting Action of the Compounds on the Germination of the Spores

First Test

The same nutrient medium as in example 7 (Czapeck medium) is used and the active material is incorporated therein in the same way.

The final concentrations (of compound according to the invention) in the nutrient medium are:

$C_0 = 0$ ppm (control)
$C_1 = 7.5$ ppm
$C_2 = 15.-$ ppm
$C_3 = 30.-$ ppm
$C_4 = 60.-$ ppm The medium thus treated is run into the cavities of was plates and left to cool and solidify. The balls of nutrient medium are contaminated by depositing on each, 50 ul of an aqueous suspension of spores of the species botyrtis cinerea or penicillium expansun. The plates are put in Petri dishes of 15 cm diameter having at the bottom a wet filter paper. They are left to incubate for 24 hours at a temperature of 22° C. After this, the ungerminated spores are counted under the microscope and the number of ungerminated spores is expressed as a percentage of the total number of spores counted. 0% signifies that all the spores have germinated, which is the case with the control, 100% that no spore has germinated, and therefore that the product has a total action.

The results obtained with the compounds of examples 1 and 2 are collected in the table II below:

Table No. II

| | PERCENTAGE OF UNGERMINATED SPORES | | | | | | | |
|---|---|---|---|---|---|---|---|---|
| Fungus | Botrytis Cinerea | | | | Pencillium Expansum | | | |
| Concentration of the product | 7.5 ppm | 15 ppm | 30 ppm | 60 ppm | 7.5 ppm | 15 ppm | 30 ppm | 60 ppm |
| Product of Example 1 | 89 | 95 | 97.5 | 100 | 100 | 100 | 100 | 100 |
| Product of Example 2 | 87 | 90 | 95 | 100 | 68 | 71 | 79 | 83 |
| Control | | 0 | | | | 0 | | |

Second Test

In this test, called the "MacCallan" test, 1 ml of suspension of spores of Alternaria tenuis and 1 ml of aqueous suspension of a compound of the invention are mixed so as to obtain in the final mixture the following concentrations of the compound according to the invention:

$C_0 = 0$ ppm (control)
$C_1 = 1.28$ ppm
$C_2 = 5.12$ ppm
$C_3 = 25$ ppm
$C_4 = 100$ ppm Drops of these mixtures are deposited in the cavities of wax plates and the plates are put in Petri dishes of 15 cm diameter, in a water saturated atmosphere. They are left to incubate for 24 hours at a temperature of 22° C. Then the percentage of ungerminated spores is counted under the microscope. 0% signifies that all the spores have germinated, 100% that no spore has germinated, therefore that the product has a total activity.

The results obtained with the compound of example 1 are tabulated in table III below:

Table No. III

| | PERCENTAGE OF UNGERMINATED SPORES | | | |
|---|---|---|---|---|
| Fungus | Alternaria Tenuis | | | |
| Concentration of the product | 1.28 ppm | 5.12 ppm | 25 ppm | 100 ppm |
| Product of Example 1 | 13.25 | 20 | 20 | 30 |
| Control | | 5.5 | | |

Third Test (Test by the Method of Inhibition Zones)

A gel-like nutrient medium (Czapeck medium) is prepared which is maintained in the fused state. In this medium are incorporated spores of the fungus penicillium expansum or botrytis cinerea. This contaminated medium is then run into Petri dishes of 10 cm diameter where it solidifies.

Suspension of product of various concentrations are prepared and are deposited at the rate of 10 $\mu l$ on pieces of filter paper of 0.4 cm diameter. These pieces of filter paper are placed on the surface of the gel-like medium. The product diffuses into the medium where it inhibits the germination of the spores thus producing around the filter paper sample halos called "zones of inhibition". The diameter of these zones of inhibition ia measured.

The results obtained with the compounds of Examples 1 and 2 are tabulated in tables IV and V below:

Table No. IV

| DIAMETER IN CM OF THE ZONES OF INHIBITION | | | | |
|---|---|---|---|---|
| Fungus | Penicillium Expansion | | | |
| Dosage of product | 0.064 $\mu g$ | 0.16 $\mu g$ | 0.4 $\mu g$ | 1 $\mu g$ |
| Product of Example 1 | 2.05 | 3.05 | 3.85 | 4.4 |
| Product of Example 2 | 1.5 | 3.5 | 4.57 | 5.4 |
| Control | | 0 | | |

Table No. V

| DIAMETER IN CM OF THE INHIBITION ZONES | | | | |
|---|---|---|---|---|
| Fungus | Botrytis Cinerea | | | |
| Dosage of product | 0.01 $\mu g$ | 0.1 $\mu g$ | 1 $\mu g$ | 10 $\mu g$ |
| Product of Example 1 | 1.11 | 1.66 | 2.30 | 2.76 |

Table No. V-continued

| DIAMETER IN CM OF THE INHIBITION ZONES | |
| --- | --- |
| Fungus | Botrytis Cinerea |
| Control | 0 |

EXAMPLE 9

Preventive Action of the Compounds Against Oidium of Barley

Aqueous suspensions of compounds of the following concentrations are prepared:

$C_0 = 0$ g/hl (control)
$C_1 = 0.156$ g/hl
$C_2 = 0.625$ g/hl
$C_3 = 2.5$ g/hl
$C_4 = 10.-$ g/hl The suspensions are sprayed on plants of "Rika" barley cultivated in pots of 250 ml and aged 12 days. The amount of suspension used per unit of surface of the pots is equivalent to 1000 l/ha. 24 hours later, after the treatment, spores of *Erysiphe graminis* were dusted on the foliage of the barley and the plants were left in a greenhouse at 22° C. for 7 days.

The number of oidium spots present on the first leaf is noted. This number indicates the level of contamination. The level of contamination of the treated plants is expressed as a percentage of the level of contamination of the control plants. 0% signifies that there is not contamination, 100% that the treated plants are as contaminated as the control plants.

The results obtained with the compounds of examples 1 and 2 are given in table VI below.

Table No. VI

| PREVENTIVE ACTION TOWARDS THE OIDIUM OF BARLEY | | | | |
| --- | --- | --- | --- | --- |
| Fungus | Erysiphe Graminis | | | |
| Concentration of the product in the suspension | 1.56 ppm | 6.25 ppm | 25 ppm | 100 ppm |
| Product of Example 1 | 100 | 100 | 28 | 2.3 |
| Product of Example 2 | 100 | 100 | 98 | 84 |
| Control | | | 100 | |

EXAMPLE 10

Study of Systemicity

A hydroponic nutrient solution is prepared (Hongland & Harnon No. 1 of pH=6). In this composition, suspensions of compounds according to the invention of concentration 100 ppm are prepared.

These suspensions are put into test tubes and into each tube there is placed a rooted plant of "Rika" barley aged 8 days, the roots extending into the liquid. These plants are left for 2 days in a room maintained at a temperature of 22° C. and at a relative atmospheric humidity of 70%.

Then a gel-like nutrient medium (Czapeck) is made (see example 7) in which spores of pencillium expansum are incorporated at 50° C. This contaminated medium is run into Petri dishes of 9 cm diameter.

Vegetation specimens 0.5 cm in length are taken from the "Rika" barley plants at the following three levels:
Level 1 = point of the sheath
Level 2 = middle of the first leaf
Level 3 = middle of the second leaf These specimens are placed in the Petri dishes at the surface of the medium containing the spores of *penicillium expansum*. If the product is systemic, it is found in the sap exuding from the plant specimens placed therein. This sap wets the surface of the nutrient medium in which the plant can migrate and inhibit the germination of the spores of *penicillium expansum* thus forming a halo surrounding the vegetation specimen. This halo is called "inhibition zone".

The presence of these inhibition zones therefore verifies that the product is systemic, i.e. that is penetrates into the fluid system of the plant. In addition, the measure of the diameter of these zones shows that there is a relation between this diameter and the concentration of compound in the initial nutrient solution into which the roots of the barley plants have been immersed. This determination is made 3 days after the deposit of the vegetation specimens on the medium.

The results obtained with the compounds of examples 1 and 2 are tabulated in table No. VII below in which the figures represent the diameter in cm of the inhibition zones.

Table No. VII

| | STUDY OF SYSTEMICITY | | |
| --- | --- | --- | --- |
| | Level of Samples | | |
| Product | Level 1 | Level 2 | Level 3 |
| Product of Example 1 | 3.25 | 3.45 | 2.25 |
| Product of Example 2 | 2.85 | 1.58 | 3.40 |
| Control | 0 | 0 | 0 |

EXAMPLE 11

Action of the Compounds Against *Erysiphe graminis* by Treatment of the Soil

Aqueous suspensions of the product of the following concentrations are made:

$C_0 = 0$ ppm (control)
$C_1 = 6.4$ ppm
$C_2 = 16$ ppm
$C_3 = 40$ ppm
$C_4 = 100$ ppm Plants of "Rika" barley are cultivated in pots of 250 ml. After the plants are aged for 8 days, the sol contained in the pots is treated with 5 ml of aqueous suspension of the product. 24 hours after the treatment spores of *Erysiphe graminis*, are dusted onto the barley plants. Six days after this operation, the spots of oidium present on the first leaf of the plants are counted. The number obtained indicates the level of contamination. The level of contamination of the treated plants is expressed as a percentge of the level of contamination of the control plants. 0% signifies that the contamination is absent, 100% that the plant is as contaminated as the control plants.

The results obtained with the compounds of example 1 are shown in table No. VIII below. These results show that the product inoculated into the treated soil is absorbed by the plant by way of the roots and passes into the flow of sap, thus conferring on the plant its resistance to *Erysiphe graminis*. The product is then endotherapic.

Table No. VIII

ACTION AGAINST THE OIDIUM OF THE BARLEY BY INJECTING THE PRODUCT INTO THE SOIL

| Fungus | Erysiphe Graminis | | | |
|---|---|---|---|---|
| Concentration of the product in the suspension | 6.4 ppm | 16 ppm | 40 ppm | 100 ppm |
| Product of Example 1 | 100 | 76 | 65.9 | 57 |
| Control | | | 100 | |

EXAMPLE 12

Action of the Compounds Against *Erysiphe graminis* by Treatment of Seeds

In this example the active substance is formulated in the form of powder for dusting, the finely divided carrier being talc and not in the form of an aqueous suspension.

The concentrations of product in the powders are the following:
$C_0 = 0$ (control)
$C_1 = 0.78\%$
$C_2 = 3.12\%$
$C_3 = 12.5\%$
$C_4 = 50\%$ The lots of seed of "Rika" barley are treated with the powder at the rate of 200 g of powder per quintal of grains and they are stirred for one and a half hour. These treated grains are sown in pots of 250 ml and these are placed in a greenhouse. Eight days layer, the sprouted plants are contaminated by dusting with spores of oidium. After 6 days of incubation, the spots of oidium present on the first leaf of each plant are counted. The level of contamination is thus determined. The level of contamination of the plants produced from the treated seed is expressed as a percentage of the level of contamination of the control plants. 0% signifies that the plant has no spot of oidium, 100% that the plant is as contaminated as the control plants.

The results relative to the compound of example 1 are tabulated in table No. IX. These results show that the product coating the seeds penetrates into the sprout or germ, is carried by the sap, and confers on the plant a resistance to *Erysiphe graminis*.

Table No. IX

| Fungus | Erysiphe Graminis | | | |
|---|---|---|---|---|
| Concentration of product in the powder | 0.78% | 3.12% | 12.5% | 50% |
| Product of Example 1 | 100 | 36 | 18 | 0 |

EXAMPLE 13

Action of the Compounds Against the Cercosporiose of the Sugar-beet

Aqueous suspensions of compounds are prepared which are applied at the rate of 1000 l/ha. The concentrations of the compounds in the suspensions are calculated so as to arrive at the following dosages of compound:
$D_0 = 0$ g/ha (control)
$D_1 = 150$ g/ha
$D_2 = 300$ g/ha The plants treated are ceres monogerm sugar-beet aged two months and cultivated in the open fields.

24 Hours after the treatment, the beets ar contaminated by spraying them with a suspension of spores of *Cerospora beticola* containing 30,000 spores/ml. 25 days after this contamination, the spots present on 5 leaves taken at random in each lot are counted and from this the average number of spots per leaf is calculated. The value 0 indicates that the product has been completely active and prevented the implantation of the fungus.

The results obtained with the compound of example 1 are presented in table No. X below:

Table No. X

ACTION ON CARCOSPORIOSE OF BEET. AVERAGE NUMBER OF SPOTS OF CEROCOSPORIOSIS PER LEAF

| Fungus | Cercospora Beticola | |
|---|---|---|
| Dose of product | 150 g/ha | 300 g/ha |
| Product of Example 1 | 0 | 0 |
| Control | 227.5 | 227.5 |

EXAMPLE 14

Action of the Compounds on the Germination of the Spores of *Ustilago maydis*

The compounds are diluted with water and to 1 ml of these dilutions is added 1 ml of a suspension of spores of *Ustilago maydis*. The dilutions are calculated so as to obtain the following concentrations of active product:
$C_0 = 0$ ppm (control)
$C_1 = 0.8$ ppm
$C_2 = 3.1$ ppm
$C_3 = 12.5$ ppm
$C_4 = 50.-$ ppm One drop of these treated suspensions is placed in the cavities of wax plates, which plates are then put into the Petri dishes of 15 cm diameter, the bottom of which is provided with a moist filter paper. The whole is stored for 24 hours at 22° C.

Then the number of sporidii per germinated spore is counted under the microscope. The results obtained with the samples treated with the compounds of the invention are compared with the results obtained with the control. The results are expressed as a percentage of inhibition of the production of sporidii. 0% signifies that there is no inhibition, i.e. that the number of sporidii emitted is the same as for the control, 100% signifies that the spores treated develop no sporidii.

The results obtained with the product of example 1 are shown in table No. XI below:

Table No. XI

ACTION ON THE SPORULATION OF USTILAGO MAYDIS

Inhibition of production of the sporidii as a percentage with respect to the untreated control

| Fungus | Ustilago Maydis | | | |
|---|---|---|---|---|
| Concentration | 0.8 ppm | 3.1 ppm | 12.5 ppm | 50 ppm |
| Product of Example 1 | 100 | 100 | 100 | 100 |
| Control | | 0 | | |

EXAMPLE 15

Action of the Compounds against *Botrytic cinerea* on Grapes

Lots of 50 grapes (Graisse variety) are treated by soaking in an aqueous dispersion of the product. These grapes are then contaminated by means of a drop of a conidien suspension applied to the opening made during the tearing away from the pedicle. 7 days after the contamination the grapes are examined and to each grape is allotted a mark according to the following scale of evaluation:

0: healthy grape
1: slight browning around the inoculum
2: browning of ¼ of the grape
3: browning of ½ of the grape
4: browning of ¾ of the grape
5: total browning of the grape The results relative to the compound of example 1 are given in the table XII below:

| Product | Concentration (in g/hl) in the dispersion | Total Rating Per Lot | Average Rating Per Grape |
|---|---|---|---|
| Product of Example 1 | 30 | 77 | 1.54 |
| Control | — | 210 | 4.20 |

EXAMPLE 16

Action of the Compounds on Acaridae Eggs

The products are diluted in water so as to obtain the following concentrations:

$C_0 = 0$ ppm (control)
$C_1 = 31.2$ ppm
$C_2 = 125.-$ ppm
$C_3 = 500.-$ ppm

Bean plants aged 15 days having two spread out cotyledonous leaves are contaminated with females of *Tetranychus urticae*. 15 females are put on per leaf. 24 hours after, these females are removed and only the eggs laid remain on the leaves.

These beans are treated by spraying, on the upper and under parts of the leaves, the dilutions indicated above. Spraying is continued until the liquid begins to run down the leaf.

15 days after the treatment, the living acaridae present on the beans are counted. The difference between the number of mites found on the control plants and on the treated plants represents the reduction of the population due to the ovicidal activity of the active material. This reduction is expressed as a percentage of the total population of the control. 0% signifies that there is no activity, 100% that the activity is complete.

The results obtained with the product of example 1 are presented in table No. XIII below:

Table No. XIII

REDUCTION OF MITE POPULATION AS A PERCENTAGE OF THE POPULATION OF THE CONTROL

| Insect | | Tetranychus Urticae | |
|---|---|---|---|
| Concentration of the product in the dilution | 31.2 ppm | 125 ppm | 500 ppm |

Table No. XIII-continued

REDUCTION OF MITE POPULATION AS A PERCENTAGE OF THE POPULATION OF THE CONTROL

| Insect | | Tetranychus Urticae | |
|---|---|---|---|
| Product of Example 1 | 3.3 | 17 | 60 |

EXAMPLE 17

Action of the Compounds on *Venturia inaequalis*, Cause of the Apple Scale

The compounds are diluted in water so as to obtain a concentration of 30 g/hl.

These suspensions are sprayed on white Calville apple trees at the rate of one spray for each 15 days period. 45 days after the first treatment the level of contamination is evaluated by counting the spotted leaves. The results are expressed as a percentage of reduction of the level of contamination with respect to the level of the control. 0% signifies that the level of contamination is the same as that of the control, 100% that the product is very effective and that the level of contamination is nil.

The results obtained with the products of examples 1 and 2 are given in table No. XIV below.

Table No. XIV

| Product | Concentration in g/hl | percentage of reduction |
|---|---|---|
| Product of Example 1 | 30 | 96 |
| Product of Example 2 | 30 | 92 |

I claim:

1. A compound which is 2-methoxycarbonylamino-3-[(1-cyano-1-phenyl)ethyl]carbamyl benzimidazole of the formula:

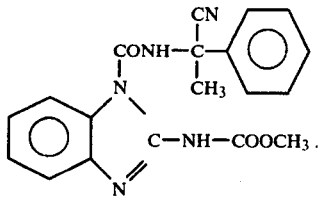

2. A compound which is 2-methoxycarbonylamino-3-[(1-cyano)cyclohexyl]carbamyl benzimidazole of the formula:

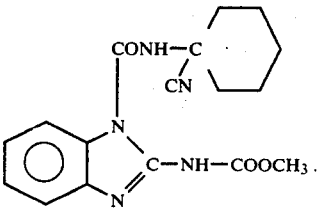

* * * * *